United States Patent
Okumura et al.

(10) Patent No.: US 10,829,377 B2
(45) Date of Patent: Nov. 10, 2020

(54) METHOD FOR PRODUCING BIS(FLUOROSULFONYL)IMIDE ALKALI METAL SALT AND METHOD FOR PRODUCING NON AQUEOUS ELECTROLYTIC SOLUTION

(71) Applicant: NIPPON SHOKUBAI CO., LTD., Osaka-shi, Osaka (JP)

(72) Inventors: Yasunori Okumura, Sulta (JP); Hiromoto Katsuyama, Sulta (JP); Naohiko Itayama, Sulta (JP); Hiroyuki Mizuno, Sulta (JP); Yukihiro Fukata, Sulta (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 71 days.

(21) Appl. No.: 16/304,589

(22) PCT Filed: May 25, 2017

(86) PCT No.: PCT/JP2017/019583
§ 371 (c)(1),
(2) Date: Nov. 26, 2018

(87) PCT Pub. No.: WO2017/204302
PCT Pub. Date: Nov. 30, 2017

(65) Prior Publication Data
US 2019/0292054 A1    Sep. 26, 2019

(30) Foreign Application Priority Data
May 27, 2016   (JP) .................. 2016-106062

(51) Int. Cl.
*C01B 21/093* (2006.01)
*H01M 10/0525* (2010.01)
*H01M 10/0568* (2010.01)
*H01M 10/0569* (2010.01)
*C01B 21/086* (2006.01)
*C07C 303/00* (2006.01)

(52) U.S. Cl.
CPC ........ *C01B 21/0935* (2013.01); *C01B 21/086* (2013.01); *C01B 21/093* (2013.01); *C07C 303/00* (2013.01); *H01M 10/0525* (2013.01); *H01M 10/0568* (2013.01); *H01M 10/0569* (2013.01); *H01M 2300/002* (2013.01)

(58) Field of Classification Search
None
See application file for complete search history.

(56) References Cited

U.S. PATENT DOCUMENTS

| | | | |
|---|---|---|---|
| 2009/0292105 A1 | 11/2009 | Michot | |
| 2011/0178306 A1 | 7/2011 | Michot | |
| 2012/0041233 A1* | 2/2012 | Sato | C01B 21/0935 564/154 |
| 2012/0232285 A1 | 9/2012 | Michot | |
| 2016/0149262 A1* | 5/2016 | Singh | H01M 10/0568 429/338 |
| 2016/0308247 A1* | 10/2016 | Buisine | H01M 10/0568 |
| 2017/0214092 A1 | 7/2017 | Okumura et al. | |

FOREIGN PATENT DOCUMENTS

| | | | | |
|---|---|---|---|---|
| CA | 2527802 A1 | 6/2007 | | |
| EP | 2257495 B1 | 7/2013 | | |
| JP | 2014201453 A | 10/2014 | | |
| JP | 2016088809 A | 5/2016 | | |
| WO | 2009123328 A1 | 10/2009 | | |
| WO | 2015082532 A1 | 6/2015 | | |
| WO | WO-2015082532 A1 * | 6/2015 | ......... | C01B 21/0935 |
| WO | 2016052752 A1 | 4/2016 | | |

OTHER PUBLICATIONS

International Search Report dated Aug. 29, 2017, which issued in the PCT Patent Application No. PCT/JP2017/019583.

* cited by examiner

*Primary Examiner* — Daniel S Gatewood
(74) *Attorney, Agent, or Firm* — Dickinson Wright PLLC

(57) ABSTRACT

Provided is a method the enables easy production of bis (fluorosulfonyl)imide suitable for a non-aqueous electrolytic solution for a lithium ion secondary battery, etc. The method for producing a bis(fluorosulfonyl)imide alkali metal salt according to the present invention comprises reacting bis (fluorosulfonyl)imide with an alkali metal compound in a reaction solution containing an organic solvent, wherein the organic solvent includes at least one organic solvent (A) selected from the group consisting of carbonate solvents, cyclic ether solvents, linear ether solvents having two or more oxygen atoms in the molecule, cyclic ester solvents, sulfolane solvents, N,N-dimethyl formamide, dimethyl sulfoxide, and N-methyl oxazolidinone.

6 Claims, No Drawings

METHOD FOR PRODUCING BIS(FLUOROSULFONYL)IMIDE ALKALI METAL SALT AND METHOD FOR PRODUCING NON AQUEOUS ELECTROLYTIC SOLUTION

TECHNICAL FIELD

The present invention relates to a method for producing a bis(fluorosulfonyl)imide alkali metal salt and a method for producing a non-aqueous electrolytic solution.

BACKGROUND ART

Bis(fluorosulfonyl)imide alkali metal salts are compounds that are useful in various applications as electrolytes for non-aqueous electrolytic solutions (herein after may be referred to as non-aqueous electrolyte solution), as additives to electrolyte solutions of fuel cells, and as antistatic agents and the like. Particularly in recent years, alkali metal batteries, specifically lithium ion secondary batteries, due to its high energy density, are used as a power source for mobile communication terminals and for portable information terminals. The market of such batteries has increased rapidly with the spread of the terminals.

As a method for producing a bis(fluorosulfonyl)imide alkali metal salt, Patent Document 1 discloses that a bis(fluorosulfonyl)imide lithium salt with a yield of 99% or more obtained by reacting an equimolar amount of bis(fluorosulfonyl)imide and lithium fluoride at 180° C. for 1 hour in an autoclave in the presence of hydrogen fluoride. However, Patent Document 1 uses a large amount of hydrogen fluoride having high corrosiveness as a solvent which makes it difficult to handle. Also, hydrogen fluoride used as the solvent is required to be removed from a product, which leaves room for improvements.

Also, Patent Document 2 discloses a method for producing an electrolytic solution material containing a specific fluorosulfonylimide salt, in which a solution containing an electrolytic solution solvent, is decompressed and/or heated to volatilize a production solvent.

PRIOR ART DOCUMENTS

Patent Documents

Patent Document 1: CA2527802A
Patent Document 2: WO2016/052752

SUMMARY OF INVENTION

Technical Problem

Accordingly, an object of the present invention is to produce a bis(fluorosulfonyl)imide alkali metal salt without using hydrogen fluoride having high corrosivity as a solvent. In addition, Patent Document 2 requires to replace a production solvent with an electrolyte solution after obtaining a bis(fluorosulfonyl)imide alkali metal salt in the production solvent, but an object of the present invention is to simplify the production method by eliminate the step.

Under these circumstances, the present invention has been made and an object thereof is to provide a method for easily producing a bis(fluorosulfonyl)imide alkali metal salt suitably used for non-aqueous electrolytic solutions such as lithium ion secondary batteries and a method for producing a non-aqueous electrolytic solution by using the bis(fluorosulfonyl)imide alkali metal salt.

Solutions to the Problems

The present invention is a method for producing a bis(fluorosulfonyl)imide alkali metal salt by reacting a bis(fluorosulfonyl)imide with an alkali metal compound in a reaction solution including an organic solvent, wherein the organic solvent includes at least one organic solvent (A) selected from the group consisting of a carbonate-based solvent, a cyclic ether-based solvent, a chain ether-based solvent having two or more of oxygen atoms within its molecule, a cyclic ester-based solvent, a sulfolane-based solvent, N,N-dimethylformamide, dimethyl sulfoxide and N-methyloxazolidinone.

The method preferably includes a mole ratio of the alkali metal compound to the bis(fluorosulfonyl)imide is 1.00 or more.

The method of the present invention is preferred to further comprising a purification step for conducting filtering a reaction solution after the reaction. The filtering a reaction solution after the reaction enables to remove the unreacted alkali metal compound.

The alkali metal compound is preferably at least one selected from the group consisting of LiCl, LiF and $Li_2CO_3$.

The organic solvent (A) is preferably the carbonate-based solvent. And the carbonate-based solvent is preferably a cyclic carbonate.

The cyclic carbonate is preferably at least one selected from the group consisting of ethylene carbonate, propylene carbonate and butylene carbonate.

The production method of the invention is preferably further comprising a volatilization operation for removing a volatile matter in the reaction solution by decompression and/or heating.

A method for producing a non-aqueous electrolytic solution of the present invention which can solve the above problems is characterized in that using a bis(fluorosulfonyl)imide alkali metal salt containing an organic solvent for preparing the non-aqueous electrolytic solution without conducting a drying step for the bis(fluorosulfonyl)imide alkali metal salt after obtaining the bis(fluorosulfonyl)imide alkali metal salt containing the organic solvent by the production method mentioned above.

Effects of the Invention

According to the present invention, the production cost of the bis(fluorosulfonyl)imide alkali metal salt can be reduced because operation of replacing a solvent after a reaction is unnecessary. Also, the method of the present invention includes a purification step for filtering a reaction solution after a reaction which enable to remove an unreacted alkali metal salt resulted in obtaining a highly-purified bis(fluorosulfonyl)imide alkali metal salt. Further, the bis(fluorosulfonyl)imide alkali metal salt by the present invention is obtained as a solution containing an organic solvent suitable for a non-aqueous electrolyte solution which enable to obtain a non-aqueous electrolyte solution without any modification or by merely diluting the solution. Therefore, the workability in the production of the non-aqueous electrolyte solution is improved which enable to produce the non-aqueous electrolytic solution easily and inexpensively.

DESCRIPTION OF EMBODIMENTS

Hereinafter, the present invention is described in more detail. In the following description, "%" is "% by mass", "part" is "part by mass" and a range of "A-B" is A or more and B or less unless otherwise noted.

The present invention is a method for producing a bis(fluorosulfonyl)imide alkali metal salt by reacting a bis(fluorosulfonyl)imide with an alkali metal compound in a reaction solution including an organic solvent, wherein the organic solvent includes at least one organic solvent (A) selected from the group consisting of a carbonate-based solvent, a cyclic ether-based solvent, a chain ether based solvent having two or more of oxygen atoms within its molecule, a cyclic ester-based solvent, a sulfolane-based solvent, N,N-dimethylformamide, dimethyl sulfoxide and N-methyloxazolidinone. Hereinafter, the reaction solution to be subjected to the purification process after completion of the reaction is referred to as "reaction solution after the reaction" or "solution after the reaction" to differentiate from a reaction solution during a reaction of or in a mixed stage of bis(fluorosulfonyl)imide, an alkali metal halide and an organic solvent.

The bis(fluorosulfonyl)imide alkali metal salt includes lithium bis(fluorosulfonyl)imide (LiFSI), sodium bis(fluorosulfonyl)imide (NaFSI), potassium bis(fluorosulfonyl)imide (KFSI) and the like. Among these examples, lithium bis(fluorosulfonyl)imide is preferred.

[Reaction Between Bis(Fluorosulfonyl)imide and an Alkali Metal Compound]

A reaction between bis(fluorosulfonyl)imide (HFSI) and an alkali metal compound is conducted in a reaction solution containing an organic solvent.

[Bis(fluorosulfonyl)imide]

Bis(fluorosulfonyl)imide can be synthesized by conventionally-known methods. For example, bis(fluorosulfonyl)imide can be synthesized from a bis(sulfonyl halide)imide by using a fluorinating agent. Examples of the halogen in bis(sulfonyl halide)imide include Cl, Br, I and At other than F.

Hereinafter, a fluorination step in which bis(fluorosulfonyl)imide is synthesized from the bis(sulfonyl halide)imide by using the fluorinating agent is described. For example, a fluorination reaction of the bis(sulfonyl halide)imide may be carried out. Specifically, methods disclosed in CA2527802A, Jean'ne m. Shreeve et al., Inorg. Chem. 1998, 37(24), 6295-6303 are exemplified. And the bis(sulfonyl halide)imide to be used as a starting material may be a commercially available product, or may be synthesized by a known method. Also, bis(fluorosulfonyl)imide may be synthesized by using urea and fluorosulfonic acid as disclosed in Japanese Domestic Re-publication of PCT publication Hei8-511274.

[Alkali Metal Compound]

The alkali metal compound in the production method of the present invention include: hydroxides such as LiOH, NaOH, KOH, RbOH and CsOH; carbonates such as $Li_2CO_3$, $Na_2CO_3$, $Rb_2CO_3$ and $Cs_2CO_3$; bicarbonates such as $LiHCO_3$, $NaHCO_3$, $KHCO_3$, $RbHC_3$ and $CsHCO_3$; chlorides such as LiCl, NaCl, KCl, RbCl and CsCl fluorides such as LiF, NaF, KF, RbF and CsF; an alcoxide compound such as $CH_3OLi$, EtOLi; an alkyllithium compound such as EtLi, BuLi and t-BuLi (wherein Et represents ethyl group and Bu represents butyl group). Among these examples, carbonates, bicarbonates, chlorides and fluorides is preferred and at least one selected from the group consisting of LiCl, LiF and $Li_2CO_3$ is more preferred as the alkali metal compound. $Li_2CO$ may generate water on the reaction with bis(fluorosulfonyl)imide and the generation of water is preferably avoided which have a harmful influence on a battery. Considering the above, LiCl and/or LiF is the most preferable among the examples. When the alkali metal compound is LiCl and/or LiF, the purification of the bis(fluorosulfonyl)imide alkali metal salt becomes easy because the boiling points of HCl and HF generated as by-product in the reaction of bis(fluorosulfonyl)imide and the alkali metal compound are low which enables to remove the by-product by a volatilization operation. Furthermore, fluorides, particularly LiF is preferred which has a sufficiently small influence on a final product battery compared to using chlorides. The hydroxide and the alcoxide compound, due to its too high basicity, may cause side reaction with the organic solvent contained in the reaction solution.

The mole ratio of the alkali metal contained in the alkali metal compound to the bis(fluorosulfonyl)imide in the reaction between bis(fluorosulfonyl)imide and the alkali metal compound is preferably 1.00 or more. The lower limit of the mole ratio is, for examples, preferably 1.00 or more, more preferably 1.01 or more, still more preferably 1.03 or more, particularly preferably 1.05 or more and particularly more preferably 1.10 or more. And the upper limit of the mole ratio is preferably 2.00 or less, more preferably 1.80 or less, still mere preferably 1.50 or less, particularly preferably 1.30 or less and particularly more preferably 1.20 or less. When the mole ratio of the alkali metal contained in the alkali metal compound to the bis(fluorosulfonyl)imide is included in the above range, an equivalent or more of the alkali metal compound is used for the reaction, the alkali metal compound is considered to become an insoluble solid in an electrolyte solution material and an unreacted alkali metal compound can be separated and purified by filtering. The bis(flourosulfonyl)imide alkali metal salt is soluble in the electrolyte solution material. Therefore, filtering the reaction solution after the reaction enables to separate and remove the bis(fluorosulfonyl)imide alkali metal salt, which is objective product and has solubility to the reaction solution after the reaction, from the unreacted alkali metal compound resided as a filter residue. Bis(fluorosulfonyl)imide cannot be removed by filtering because bis(fluorosulfonyl)imide is in a liquid state instead of in a solid state at normal temperature and filtering temperatures. However, the removal operation of bis(fluorosulfonyl)imide may possibly be simplified if the mole ratio of the alkali metal contained in the alkali metal compound to bis(fluorosulfonyl)imide is included in this range and reaction conditions are appropriately set which enable to reduce the amount of bis(fluorosulfonyl)imide contained after the reaction.

In the production method of the present invention, the amount of the bis(fluorosulfonyl)imide to be used in the reaction is preferably 10 to 70% by weight relative to the total reaction solution. The lower limit of the bis(fluorosulfonyl)imide is preferably 15% by weight or more and more preferably 20% by weight or more. The upper limit of the bis(fluorosulfonyl)imide is preferably 60% by weight or lower, more preferably 50% by weight or lower. When the amount of the bis(fluorosulfonyl)imide to the total reaction solution is included in the above range, a generated bis(fluorosulfonyl)imide alkali metal salt is soluble and an excess alkali metal compound used in the reaction can be removed by filtering.

In the production method of the present invention, the amount of the alkali metal compound to be used in the reaction is preferably 0.1 to 50% by weight relative to the total reaction solution. The lower limit of the alkali metal compound is more preferably 0.5% by weight or more, still more preferably 1% by weight or more. The upper limit of the alkali metal compound is preferably 40% by weight or lower, more preferably 30% by weight or lower, still more preferably 20% by weight or lower, particularly preferably 15% by weight or lower and most preferably 10% by weight or lower. When the amount of the alkali metal compound to the total reaction solution is included in the above-range, the reaction between bis(fluorosulfonyl)imide and the alkali metal compound proceeds sufficiently. And a bis(fluorosulfonyl)imide alkali salt solution can be obtained by removing the excessively used alkali metal compound by filtering the reaction solution after the reaction.

[Organic Solvent Used for the Reaction]

The organic solvent used in the production method of the present invention includes the above-mentioned organic solvent (A) and the organic solvent can includes another organic solvent other than the organic solvent (A).

The organic solvent (A) used in the production method of the present invention is preferably at least one selected from the group consisting of a carbonate-based solvent, a cyclic ether-based solvent, a chain ether based solvent having two or more of oxygen atoms within its molecule, a cyclic ester-based solvent, a sulfolane-based solvent, N,N-dimethylformamide, dimethyl sulfoxide and N-methyloxazolidinone.

Noted that the organic solvent (A) can be used as a solvent for the electrolyte solution material without any modifications, the organic solvent (A) may be referred to as an electrolyte solution solvent in the present specification.

Specific examples of the organic solvent (A) include: a carbonate-based solvent, such as ethylene carbonate, propylene carbonate, butylene carbonate, dimethyl carbonate, ethylmethyl carbonate and diethyl carbonate;
a linear ether-based solvent having two or more of oxygen atoms within its molecule, such as dimethoxymethane and 1,2-dimethoxyethane;
a cyclic ether-based solvent, such as tetrahydrofuran, 2-methyltetrahydrofuran, 1,3-dioxane and 4-methyl-1,3-dioxolane;
a cyclic ester-based solvent, such as γ-butyrolactone and γ-valerolactone;
a sulfolane-based solvent, such as sulfolane and 3-methylsulfolane; and N,N-dimethylformamide dimethyl sulfoxide and N-methyloxazolidinone.

Among these exemplified solvents, the carbonate-based solvent such as ethylene carbonate, propylene carbonate, butylene carbonate, dimethyl carbonate, ethylmethyl carbonate and the diethyl carbonate (particularly a cyclic carbonate such as ethylene carbonate, propylene carbonate and butylene carbonate) and the cyclic ester-based solvent such as γ-butyrolactone and γ-valerolactone are preferred, the carbonate-based solvent is particularly preferred and a cyclic carbonate is most preferred as the organic solvent (A). These solvents may be used singly, or two or more of them may be used in the form of a mixture.

In the production method of the present invention, the content of the organic solvent to the total reaction solution is preferably 30 to 90% by weight. The lower limit of the organic solvent content is more preferably 40% by weight or more, still more preferably 50% by weight or more. The upper limit of the organic solvent content is more preferably 85% by weight or lower and still more preferably 80% by weight or lower. When the content of the organic solvent to the total reaction solution is included in the above range, a generated bis(fluorosulfonyl)imide alkali metal salt is soluble and an excess alkali metal compound used in the reaction can be removed by filtering. And in the production method of the present invention, the content of the organic solvent (A) to the total reaction solution is preferably 30 to 90% by weight. The lower limit of the organic solvent (A) contained is more preferably 40% by weight or more, still more preferably 50% by weight or more. The upper limit of the organic solvent (A) contained is more preferably 85% by weight or lower and still more preferably 80% by weight or lower. When the content of the organic solvent (A) to the total reaction solution is included in the above range, a generated bis(fluorosulfonyl)imide alkali metal salt is soluble and an excess alkali metal compound used in the reaction can be removed by filtering.

In the production method of the present invention, the content of the organic solvent (A) to the total organic solvent in the reaction solution is preferably 30 to 100% by weight. The lower limit of the organic solvent content is more preferably 60% by weight or more, still more preferably 90% by weight or more, and most preferably 100% by weight. When the content of the organic solvent (A) to the total organic solvent is included in the above range, a generated bis(fluorosulfonyl)imide alkali metal salt is soluble and an excess alkali metal compound used in the reaction can be removed by filtering.

The specific examples of another organic solvent other than the organic solvent (A) include an alcohol-based solvent, such as methanol, ethanol, propanol and butanol; a carboxylic acid-based solvent, such as formic acid and acetic acid; a ketone, such as acetone, methyl ethyl ketone, methyl isobutyl ketone and diisobutyl ketone; a nitrile-based solvent, such as isobutyronitrile, acetonitrile, valeronitrile and benzonitrile; a chain ester-based solvent, such as ethyl acetate, isopropyl acetate and butyl acetate; a chain ether-based solvent having one oxygen atom within its molecule, such as diethyl ether, diisopropyl ether, t-butyl methyl ether and cyclopentyl methyl ether; a nitro-group-containing solvent, such as nitromethane and nitrobenzene; N-methylpyrrolidone; and a glyme-based solvent.

The order of addition of materials in the reaction between bis(fluorosulfonyl)imide and the alkali metal compound is not particularly limited. The reaction can be conducted while adding the alkali metal compound to the mixture of the organic solvent and bis(fluorosulfonyl)imide, or the reaction can be conducted while adding bis(fluorosulfonyl)imide to the mixture of the organic solvent and the alkali metal compound. Also, the reaction can be conducted while adding the mixture of the organic solvent and the alkali metal compound to the mixture of the organic solvent and bis(fluorosulfonyl)imide, or the reaction can be conducted while adding the mixture of the organic solvent and bis(fluorosulfonyl)imide to the mixture of the organic solvent and the alkali metal halide. It is also possible to initiate the reaction after mixing bis(fluorosulfonyl)imide, the alkali metal compound and the organic solvent. And an additional method is not particularly limited, but the method is exemplified as one time addition method for adding required amount at once, a batch-type addition method for adding required amount by divided into several times, and a sequentially addition method for adding materials continuously to the required amount.

[Reaction Conditions]

Reaction conditions for the reaction between bis(fluorosulfonyl)imide and the alkali metal compound in the reaction solution including the organic solvent, particularly including the organic solvent (A) is described below.

The reaction temperature of the reaction between bis(fluorosulfonyl)imide and the alkali metal compound (the "reaction temperature" is, for examples, the temperature of the reaction solvent in the examples below) can be set to 10 to 100° C. The upper limit of the reaction temperature is preferably 80° C. or lower and more preferably 60° C. or lower. The lower limit, of the reaction temperature is preferably 10° C. or higher, more preferably 20° C. or higher. The reaction temperature is not limited to above temperature range. Low reaction temperatures may reduce the reaction rate and high reaction temperatures may generate impurities, thus they are undesirable.

The pressure of the reaction between bis(fluorosulfonyl)imide and the alkali metal compound can be performed under high pressure, normal pressure or reduced pressure. The degree of the reaction pressure is preferably 1250 hPa or lower, more preferably 1150 hPa or lower, and still more preferably 1050 hPa or lower. The lower limit of the reaction pressure can set to about 800 hPa.

The reaction time (i.e., mixing time in the reaction) can be set to, for example, 0.1 to 24 hours, preferably 0.5 to 12 hours and more preferably 1 to 8 hours.

[Volatilization Operation]

The production method of the present invention preferably includes a volatilization operation by normal pressure, reduced pressure and/or heating for removing a volatile matter in the reaction solution. The production method of the present invention preferably includes the volatilization operation for removing the volatile matter in the reaction solution by reduced pressure and/or heating. The volatile matter such as hydrogen halide, water, carbon dioxide and the like is generated as by-product in the reaction solution. The volatilization operation for removing the volatile matter in the reaction solution by normal pressure, reduced pressure and/or heating can be conducted during the reaction or after the reaction.

In the reaction between bis(fluorosulfonyl)imide and the alkali metal compound, if the alkali metal compound is LiCl and/or LiF, a by-product is easily removed by the volatilization operation because HCl and HF which are the volatile matter generated as a by-product by the reaction between bis(fluorosulfonyl)imide and the alkali metal compound has a low boiling point. As a result, the reaction proceeds in favor of the product side more and the purification of the bis(fluorosulfonyl)imide alkali metal salt is conducted easily.

The volatilization operation is not particularly limited, and may be performed either under normal pressure or reduced pressure. From the viewpoint of avoiding the decomposition of the bis(fluorosulfonyl)imide alkali metal salt by heating and promoting volatilization efficiently, the volatilization operation is desirably performed under reduced pressure out of normal pressure, reduced pressure and heating. When conducting the volatilization under reduced pressure, a degree of reduction in pressure is not particularly limited, and can be adjusted appropriately depending on the types of the volatile matters, particularly depending on the types of the hydrogen halides. For example, the degree of reduction in pressure is preferably 800 hPa or lower, more preferably 40 kPa or lower (400 hPa or lower), still more preferably 15 kPa or lower (150 hPa or lower), particularly preferably 5 kPa or lower (50 hPa or lower). The lower limit of the degree of reduction can be about 10 hPa.

A volatilization temperature is not particularly limited, and can be adjusted appropriately depending on the degree of reduction in pressure, the types of the volatile matters and the types of the organic solvents. From the viewpoint of avoiding the decomposition of the bis(fluorosulfonyl)imide alkali metal salt by heat, the volatilization step is desirably performed at relatively low temperatures. For example, the volatilization temperatures are preferably 10 to 110° C., more preferably 15 to 80° C., still more preferably 20 to 60° C., particularly preferably 20 to 50° C.

A time for the volatilization is not particularly limited, and can be adjusted appropriately depending on the degree of reduction in pressure, the heating temperature, the amount of the volatile matter, the amount of the organic solvent and the like. For example, the time for the volatilization is preferably 0.1 to 24 hours, more preferably 0.5 to 12 hours, still more preferably 1 to 8 hours, particularly preferably 2 to 5 hours.

A device to be used for the volatilization step and capable of achieving the decompression and/or heating may be selected appropriately depending on the volume of the solution, the degree of reduction in pressure, the heating temperature and the like. For example, a tank-type reactor and a tank-type reactor which is capable of reducing an internal pressure can be mentioned. The volatilization operation can be conducted by using a different reactor from the reactor used for the reaction. From the view point of conveniences, the reactor used for the reaction is preferably used for the volatilization operation.

The production method of the present invention can include a purification step for conducting filtering. Particularly, it is preferable to include a purification step for filtering the reaction solution obtained after the reaction. As mentioned above, the mole ratio of the alkali metal contained in the alkali metal compound to the bis(fluorosulfonyl)imide in the reaction between bis(fluorosulfonyl)imide and the alkali metal compound is preferably 1.00 or more. When the mole ratio of the alkali metal contained in the alkali metal compound to the bis(fluorosulfonyl)imide is included in the above range, an equivalent or more of the alkali metal compound is used for the reaction, the alkali metal compound is considered to become an insoluble solid in the electrolyte solution material and the unreacted alkali metal compound can be separated and purified by filtering. Accordingly, filtering the reaction solution after the reaction enables to separate the bis(fluorosulfonyl)imide alkali metal salt, which is objective product, dissolved in the reaction solution from the solid alkali metal compound in the reaction solution as a filter residue.

As a filtering method, pressure filtration and suction filtration are exemplified. The preferable conditions for the filtering is as follows: As the usable filter medium a filter made of, a fluororesin such as PTFE, a stainless steel fiber, polyolefin such as polyethylene, ultra high density polyethylene, nylon, a cellulose fiber, a glass fiber, a silica fiber, polycarbonate, cotton, polyether sulfone, cellulose acetate are exemplified. Among these examples, more preferable examples are a fluororesin, a stainless steel fiber, polyethylene and cellulose fiber, and still more preferable examples are a fluororesin, a stainless steel fiber and cellulose fiber. The retained particle diameter of the filter medium is preferably 0.05 to 50 μm, more preferably 0.1 to 10 μm, still more preferably 0.2 to 5 μm.

The filtering temperature (the temperature of the solution to be filtered after the reaction) is set to 0 to 70° C., preferably 0 to 50° C. and more preferably 20 to 50° C.

The filtering step may be operated by one step filtering or multistage filtering of two or more stages. The retained particle diameter of filter medium for a one step filtering is preferably 0.05 to 50 μm, more preferably 0.1 to 10 μm. And the retained particle diameter of filter medium for a two stage filtering is preferably 5 to 50 μm, more preferably 10 to 40 μm for the first stage and 0.05 to 20 μm, more preferably 0.05 to 5 μm for the second stage.

Washing is preferably operated after the filtering. Washing can suppress the remained bis(fluorosulfonyl)imide alkali metal salt, which is a target substance, on the filter and can increase the yield of the bis(fluorosulfonyl)imide alkali metal salt. Already mentioned organic solvent (A) is preferred as the solvent used for the washing.

An organic solvent (additional organic solvent) other than the organic solvent contained in the reaction solution can be added before and/or after the purification step for conducting the filtering. Examples as the organic solvent other than the organic solvent contained in the reaction solution include the organic solvent (A) other than the organic solvent used for the reaction. Also, a concentration operation by volatilization of the organic solvent contained in the reaction solution can be performed by decompression and/or heating before and/or after the purification step for conducting the filtering. The purification step can includes, in addition to the filtering, publicly known operations such as solid precipitation e.g., crystallization; distillation; and concentration.

[Electrolyte Solution Material Containing the Bis(fluorosulfonyl)imide Alkali Metal Salt]

The bis(fluorosulfonyl)imide alkali metal salt by the present invention is obtained as a solution containing an organic solvent suitable for a non-aqueous electrolyte solution and can be used as an electrolyte material. Also, a non-aqueous electrolyte solution can be produced from the electrolyte material without any modification or by merely diluting the electrolyte material. Also, in the case of making the bis(fluorosulfonyl)imide alkali metal salt powdered, a drying step and a pulverizing step is necessarily to be provided in the production method. However these steps are not necessary to be provided when the bis(fluorosulfonyl)imide alkali metal salt is in the liquid state mentioned above which enable to achieve simplifying a manufacturing process. In addition, in the case of drying the bis(fluorosulfonyl)imide alkali metal salt, the (fluorosulfonyl) imide alkali metal salt easily captures the organic solvent and moisture in the reaction solution resulted in difficulty to attain sufficient dryness. However, the bis(fluorosulfonyl)imide alkali metal salt in the liquid state avoids these problems. Furthermore, the bis(fluorosulfonyl)imide alkali metal salt in the liquid state is easily treated as compared to its powder state. Still more, exposure to the atmosphere during transferring work of the bis(fluorosulfonyl)imide alkali metal salt in the liquid state is much less compared to that in the powder state.

The concentration of the bis(fluorosulfonyl)imide alkali metal salt to be contained in the electrolyte solution material is not limited particularly, and can be adjusted appropriately depending on the types of the electrolyte solvents. For example, the concentration of the bis(fluorosulfonyl)imide alkali metal salt is preferably 15 to 95% by mass, more preferably 20 to 90% by mass, still more preferably 30 to 90% by mass. In the production of a non-aqueous electrolyte solution by adding the organic solvent to the electrolyte solution material, from the viewpoint of appropriately setting the concentration of the electrolyte salt in the non-aqueous electrolyte solution, the concentration of the bis(fluorosulfonyl)imide alkali metal salt to be contained in the electrolyte solution material is preferably 30% by mass or more, more preferably 40% by mass or more, still more preferably 50% by mass or more. When the electrolyte solution material according to the present invention contains the bis(fluorosulfonyl)imide alkali metal salt at a concentration of 30% by mass or more, good stability of the bis(fluorosulfonyl)imide alkali metal salt can be achieved and the generation of HF (hydrofluoric acid), which can cause the corrosion of a container for storage or transport use, can be prevented, and therefore this concentration is also suitable for the storage and transportation of the bis(fluorosulfonyl)imide, alkali metal salt.

Above-mentioned organic solvent (A) can be used as the organic solvent (A) contained in the electrolyte solution material of the present invention. The carbonate-based solvent such as ethylene carbonate, propylene carbonate, butylene carbonate, dimethyl carbonate, ethylmethyl carbonate and the diethyl carbonate (particularly a cyclic carbonate such as ethylene carbonate, propylene carbonate and butylene carbonate); and the cyclic ester-based solvent such as γ-butyrolactone and γ-valerolactone are preferred, the carbonate-based solvent is particularly preferred and the cyclic carbonate is most preferred as the organic solvent (A).

The electrolyte solution material produced by the production method according to the present invention can be used suitably as a material for an ionic conductor that constitutes a primary battery, a battery having a charge/discharge mechanism, such as a lithium ion secondary battery and a fuel cell or an electrical storage device (an electrochemical device) such as an electrolytic capacitor, an electric double-layer capacitor and a solar cell, and an electrochromic display element.

The present invention also includes, within the scope thereof; a non-aqueous electrolyte solution produced using the electrolyte solution material; and a method for producing a non-aqueous electrolyte solution using the electrolyte solution material. A non-aqueous electrolyte solution can be produced by mixing a non-aqueous electrolyte solution preparation solvent with the electrolyte solution material, if necessary. In the non-aqueous electrolyte solution, various types of electrolytes, additives and the like may be added for the purpose of improving battery properties. It is also possible to add a solvent suitable for the dissolution of an electrolyte or the like to the electrolyte solution material. In the preset invention, the non-aqueous electrolyte can be prepared by adding a desired solvent to the electrolyte solution material.

The electrolyte solution preparation solvent to be used is not particularly limited, as long as the solvent is compatible with the organic solvent (A) and can dissolve and disperse a desired electrolyte salt therein. In the present invention, any one of the conventional known solvents for batteries can be used. In the electrolyte solution material, the organic solvent (A) is contained. If required, the electrolyte solution material may additionally be added a solvent that is of the same type as the organic solvent (A), that is, the organic solvent (A) other than the organic solvent (A) already used. Any one of the above-mentioned organic solvent (A) may be used as the solvent. The temperature of the electrolyte solution preparation solvent is not particularly limited. The temperature may be room temperature, or may be adjusted appropriately as required.

The electrolyte solution preparation solvent is exemplified below including the above-mentioned organic solvent (A). That is, the solvent includes: an ether solvent such as ethylene glycol dimethyl ether, ethylene glycol diethyl ether, tetrahydrofuran, 2-methyltetrahydrofuran, 2,6-dimethyltetrahydrofuran, tetrahydropyran, crown ether, triethylene glycol dimethyl ether, tetraethylene glycol dimethyl ether, 1,4-dioxane and 1,3-dioxolan; a chain carbonate ester solvent such as dimethyl carbonate, ethyl methyl carbonate, diethyl carbonate, diphenyl carbonate and methyl phenyl carbonate; a cyclic carbonate solvent such as ethylene carbonate, propylene carbonate, 2,3-dimethylethylene carbonate, butylene carbonate, vinylene carbonate, 2-vinylethylene carbonate; an aromatic carboxylate ester solvent such as methyl benzoate and ethyl benzoate: a lactone solvent such as γ-butyrolactone, γ-valerolactone and δ-valerolactone; a phosphate ester solvent such as trimethyl phosphate, ethyl dimethyl phosphate, diethyl methyl phosphate and triethyl phosphate; a nitrile solvent such as acetonitrile, propionitrile, methoxypropionitrile, glutaronitrile, adiponitrile, 2-methylglutaronitrile, valeronitrile, butyronitrile and isobutyronitrile; a sulfur compound solvent such as dimethyl sulfone, ethyl methyl sulfone, diethyl sulfone, sulfolane, 3-methylsulfolane and 2,4-dimethylsulfolane; an aromatic nitrile solvent such as benzonitrile and tolunitrile; nitromethane, 1,3-dimethyl-2-imidazolidinone, 1,3-dimethyl-3,4,5,6-tetrahydro-2(1H)-pyrimidinone, 3-methyl-2-oxazolidinone and the like.

Among the electrolyte solution preparation solvents, the carbonate ester (a carbonate-based solvent) such as the linear carbonate ester and the cyclic carbonate ester, the lactone and the ether are preferred; dimethyl carbonate, ethylmethyl carbonate, diethyl carbonate, ethylene carbonate, propylene carbonate, γ-butyrolactone, γ-valerolactone and the like are more preferred; and the carbonate-based solvent such as dimethyl carbonate, ethylmethyl carbonate, diethyl carbonate, ethylene carbonate and propylene carbonate is still more preferred. These solvents may be used singly, or two or more of them may be used in combination.

In the present invention, if necessary, an electrolyte salt that is different from the bis(fluorosulfonyl)imide alkali metal salt (also referred to as "another electrolyte salt", hereinafter) may be mixed with the electrolyte solution material. Above-mentioned another electrolyte salt may be added to the electrolyte solution material to which the electrolyte solution preparation solvent is not added yet. From the viewpoint of the dissolution efficiency of above-mentioned another electrolyte salt, it is desirable to add above-mentioned another electrolyte salt after the addition of the electrolyte solution preparation solvent to the electrolyte solution material. For example, in the case where above-mentioned another electrolyte salt to be added is poorly soluble in ethylene carbonate, like $LiPF_6$, it is desirable to add the electrolyte salt after the addition of a solvent suitable for the dissolution of the electrolyte salt, as the electrolyte solution preparation solvent, to the electrolyte solution material.

Above-mentioned another electrolyte salt is not particularly limited, and may be any one of the conventional known electrolytes that may be used in electrolytes for lithium ion secondary batteries. As above-mentioned another electrolyte salt, such an electrolyte salt is exemplified by an inorganic cation salt and organic cation salt of trifluoromethanesulfonate ion ($CF_3SO_3^-$), hexafluorophosphate ion ($PF_6^-$), perchlorate ion ($ClO_4^-$), tetrafluoroborate ion ($BF_4^-$), hexafluoroarsenate ion ($AsF_6^-$), tetracyanoborate ion ($[B(CN)_4]^-$), tetrachloroaluminum ion ($AlCl_4^-$), tricyanomethide ion ($C[(CN)_3]^-$), dicyanamide ion ($N[(CN)_2]^-$), tris(trifluoromethanesulfonyl)methide ion ($C[(CF_3SO_2)_3]^-$), hexafluoroantimonate ion ($SbF_6^-$) and dicyanotriazolate ion (DCTA) as an anion; a fluorosulfonylimide salt other than the bis(fluorosulfonyl)imide alkali metal salt. Specific examples include $LiPF_6$, $LiPF_3(C_2F_5)_3$, $LiBF_4$, $LiBF(CF_3)_3$, preferably $LiPF_6$ or $LiBF_4$, and more preferably $LiPF_6$. When the electrolyte solution preparation solvent and above-mentioned another electrolyte salt are mixed with the electrolyte solution material according to the present invention to produce the non-aqueous electrolyte solution, the generation of heat during the mixing of the electrolyte salt can be prevented, and therefore the decomposition of the non-aqueous electrolyte solution can be prevented, resulting in the production of the electrolyte solution having good quality.

When the non-aqueous electrolyte solution contains above-mentioned another electrolyte salt, the amount of another electrolyte salt is not particularly limited as long as the total concentration of above-mentioned another electrolyte salt and the bis(fluorosulfonyl)imide alkali metal salt is equal to a saturated concentration or lower. The content of above-mentioned another electrolyte salt is preferably 0.1 mol/L or more, more preferably 0.3 mol/L or more, still more preferably 0.8 mol/L or more and preferably 2.5 mol/L, or less, more preferably 2.0 mol/L or less and still more preferably 1.5 mol/L or less.

The ratio between the bis(fluorosulfonyl)imide alkali metal salt and above-mentioned another electrolyte salt is not particularly limited. Therefore, the ratio between the bis(fluorosulfonyl)imide alkali metal salt and above-mentioned another electrolyte salt may be the same, or one of them may be higher. The proportion of above-mentioned another electrolyte salt may be higher than the bis(fluorosulfonyl)imide alkali metal salt. To obtain a further excellent resistance to short circuit prevention and an effect of improving the capacity retention rate (cycle properties) at the time of charging and discharging by increasing the concentration ratio of the bis(fluorosulfonyl)imide alkali metal salt, the preferable concentration ratio is bis(fluorosulfonyl)imide alkali metal salt:above-mentioned another electrolyte salt=1:3 to 3:1 and more preferably 1:2 to 2:1.

When the non-aqueous electrolyte solution contains above-mentioned another electrolyte salt, it is not particularly limited as long as the total concentration of above-mentioned another electrolyte salt and the bis(fluorosulfonyl)imide alkali metal salt is equal to a saturated concentration or lower. The concentration of above-mentioned another electrolyte salt is preferably 0.5 mol/L or more, more preferably 0.8 mol/L or more, still more preferably 1.0 mol/L or more and preferably 3.0 mol/L or less, more preferably 2.0 mol/L or less and still more preferably 1.5 mol/L or less.

The non-aqueous electrolytic solution of the present invention may contain an additive to improve various properties of the lithium ion secondary battery. The additive may be added at any stages in the process of manufacturing the non-aqueous electrolytic solution, and is not particularly limited and, for example, the additive may be added after the addition of the electrolyte salt.

The additive is exemplified by a cyclic carbonate having a unsaturated bond, such as vinylene carbonate (VC), vinylethylene carbonate (VEC), methylvinylene carbonate (MVC) and ethylvinylene carbonate (EVC); a carbonate compound such as fluoroethylene carbonate, trifluoropropylene carbonate, phenylethylene carbonate and erythritan carbonate; a carboxylic acid anhydride such as succinic anhydride, glutaric anhydride, maleic anhydride, citraconic anhydride, glutaconic anhydride, itaconic anhydride, diglycolic anhydride, cyclohexanedicarboxylic anhydride, cyclopentanetetracarboxylic dianhydride and phenylsuccinic anhydride; a sulfur-containing compound such as ethylene sulfite, 1,3-propanesultone, 1,4-butanesultone, methyl methanesulfonate, busulfan, sulfolane, sulfolane, dimethyl sulfone, tetramethylthiuram monosulfide and trimethylene glycol sulfate ester; a nitrogen-containing compound such as 1-methyl-2-pyrrolidinone, 1-methyl-2-piperidone, 3-methyl-2-oxazolidinone, 1,3-dimethyl-2-imidazolidinone and N-methylsuccinimide; a phosphate such as monofluorophosphate and difluorophosphate; a saturated hydrocarbon compound such as heptane, octane and cycloheptane.

The concentration of the above-described additive in 100% by mass of the non-aqueous electrolyte solution is preferably 0.1% by mass or more, more preferably 0.2% by mass or more, still more preferably 0.3% by mass or more and 10% by mass or less, more preferably 8% by mass or less and still more preferably 5% by mass or less. When the usage amount of the additive is too small, it may be possibly difficult to obtain an effect by the additive in some cases. Alternatively, even when a large amount of the additive is used, an effect commensurate with added amount may be hardly obtained and conductivity may be possibly decreased due to high viscosity of the non-aqueous electrolyte solution.

It is noted that non-aqueous electrolyte solution 100% by mass means the sum of all the components contained in the non-aqueous electrolyte solution such as the above-mentioned bis(fluorosulfonyl)imide alkali metal salt, above-mentioned another electrolyte salt, the solvent, and optionally used additives.

reaction, a solution after the reaction was concentrated under reduced pressure at 50° C. for 1 hour at approximately 50 to 100 hPa and then filtered under reduced pressure using PTFE filter paper (retained particle diameter 1 μm) to obtain 18.7 g of dimethyl carbonate solution containing 9.35 g of LiFSI [bis(fluorosulfonyl)imide lithium salt]. The amount of LiFSI was determined by F-NMR.

Examples 2 to 5

LiFSI in each example was obtained by the same manner as in Example 1 except that the raw materials in Table 1 were used and the production conditions in Table 1 were employed. The content of the obtained LiFSI and the amount of the solution after the reaction were as shown in Table 1. In Table 1, "DMC" represents dimethyl carbonate, "EMC" represents ethyl methyl carbonate, "EC" represents ethylene carbonate and "PC" represents propylene carbonate.

TABLE 1

|  |  |  |  | Example 2 | Example 3 | Example 4 | Example 5 |
|---|---|---|---|---|---|---|---|
| Raw Materials | Alkali Metal Compound | LiF | g(mmol) | — | 1.43(55.2) | 1.43(55.2) | 1.43(55.2) |
|  |  | LiCl | g(mmol) | 2.33(55.0) | — | — | — |
|  | HFSI |  | g(mmol) | 9.05(50.0) | 9.05(50.0) | 9.05(50.0) | 9.05(50.0) |
|  | Organic Solvent | DMC | g | 20 | — | — | — |
|  |  | EMC | g | — | 20 | — | — |
|  |  | EC | g | — | — | 20 | — |
|  |  | PC | g | — | — | — | 20 |
|  | TOTAL |  | g | 31.4 | 30.5 | 30.5 | 30.5 |
| Production Conditions | Reaction Temperature |  | ° C. | 25 | 25 | 45 | 45 |
|  | Temperature Under Decompression |  | ° C. | 50 | 55 | 80 | 80 |
| Products | LiFSI |  | g(mmol) | 9.26(49.5) | 9.30(49.7) | 9.27(49.7) | 9.27(49.5) |
|  | Solution After The Reaction |  | g | 17.3 | 18.7 | 29.29 | 29.24 |

The present application claims the benefit of the priority date of Japanese patent application No. 2016-106062 filed on May 27, 2016. All of the contents of the Japanese patent application No. 2016-106062 filed on May 27, 2016 are incorporated by reference herein.

EXAMPLES

Hereinafter, the present invention is described in detail with Examples. However, the present invention is not limited to the following Examples in any way, and it is possible to carry out the present invention according to the Examples with an additional appropriate change within the range of the above descriptions and the following descriptions. Such a change is also included in the technical scope of the present invention.

Example 1

In a PFA (fluororesin) made reaction container, 1.43 g (55 mmol) of LiF and 20 g of dimethyl carbonate were weighed and introduced. 9.05 g (50 mmol) of HFSI [bis(fluorosulfonyl)imide] was introduced into the reaction container. Thereafter, the reaction solution was stirred at 25° C. under atmospheric pressure for 5 hours for reaction. After the Comparative Example 1

In a PFA (fluororesin) made reaction container, 1.43 g (55 mmol) of LiF and 20 g of acetonitrile were weighed and introduced. 9.05 g (50 mmol) of HFSI [bis(fluorosulfonyl) imide] was introduced into the reaction container. Thereafter, the reaction solution was stirred at 25° C. under atmospheric pressure for 5 hours for reaction. A solution after the reaction was centrifuged to remove solids. And thus obtained solution was concentrated under reduced pressure at 50° C. for 1 hour at approximately 50 to 100 hPa to obtain 9.35 g of LiFSI [bis(fluorosulfonyl)imide salt].

It was confirmed by gas chromatography that acetonitrile as impurities remained in the product.

INDUSTRIAL APPLICABILITY

The bis(fluorosulfonly)imide alkali metal salt produced by the production method according to the present invention can be used suitably as a material for an ionic conductor that constitutes a primary battery, a battery having a charge/discharge mechanism such as a lithium ion secondary battery and a fuel cell or an electrical storage device (an electrochemical device) such as an electrolytic capacitor, an electric double-layer capacitor, a solar cell and an electrochromic display element.

The invention claimed is:

1. A method for producing a bis(fluorosulfonyl)imide alkali metal salt by reacting a bis(fluorosulfonyl)imide with an alkali metal compound in a reaction solution including an organic solvent, wherein the alkali metal compound is LiCl and/or LiF, a mole ratio of the alkali metal compound to the bis(fluorosulfonyl)imide is 1.00 or more, and removing a volatile matter in the reaction solution by a volatilization operation including decompression and/or heating, wherein
the organic solvent includes at least one organic solvent (A) selected from the group consisting of a carbonate-based solvent, a cyclic ether-based solvent, a chain ether-based solvent having two or more of oxygen atoms within its molecule, a cyclic ester-based solvent, a sulfolane-based solvent, N,N-dimethylformamide, dimethyl sulfoxide and N-methyloxazolidinone.

2. The method for producing the bis(fluorosulfonyl)imide alkali metal salt according to claim 1,
further comprising a purification step by conducting filtering of a reaction solution after the reaction.

3. The method for producing the bis(fluorosulfonyl)imide alkali metal salt according to claim 1, wherein
the organic solvent (A) is the carbonate-based solvent.

4. The method for producing the bis(fluorosulfonyl)imide alkali metal salt according to claim 3, wherein
the carbonate-based solvent is a cyclic carbonate.

5. The method for producing the bis(fluorosulfonyl)imide alkali metal salt according to claim 4, wherein
the cyclic carbonate is at least one selected from the group consisting of ethylene carbonate, propylene carbonate and butylene carbonate.

6. A method for producing a non-aqueous electrolytic solution, wherein
using a bis(fluorosulfonyl)imide alkali metal salt containing an organic solvent for preparing the non-aqueous electrolytic solution without conducting a drying step for the bis(fluorosulfonyl)imide alkali metal salt after obtaining the bis(fluorosulfonyl)imide alkali metal salt containing the organic solvent by the production method according to claim 1.

* * * * *